(12) United States Patent
Buckner, III et al.

(10) Patent No.: US 6,502,320 B2
(45) Date of Patent: Jan. 7, 2003

(54) APPARATUS AND METHOD FOR MEASURING ALIGNMENT OF METERED DOSE INHALER VALVES

(75) Inventors: Charles Amick Buckner, III, Durham, NC (US); John Anderson Mascho, Jr., Clayton, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/136,093

(22) Filed: May 1, 2002

(65) Prior Publication Data

US 2002/0152628 A1 Oct. 24, 2002

Related U.S. Application Data

(63) Continuation of application No. 09/561,232, filed on Apr. 28, 2000, now Pat. No. 6,415,526.

(51) Int. Cl.[7] .............................................. G01B 11/14

(52) U.S. Cl. ....................... 33/286; 33/522; 33/DIG. 21

(58) Field of Search ................................ 33/1 BB, 286, 33/501.02, 501.05, 522, 613, 645, 813, 819, 831, DIG. 21; 73/865.8; 356/3, 3.01, 3.02, 3.03, 4.01

(56) References Cited

U.S. PATENT DOCUMENTS

| 2,508,251 | A |   | 5/1950 | Ingle ........................ 33/501.02 |
|---|---|---|---|---|
| 3,073,034 | A |   | 1/1963 | Antoszewski ................. 33/522 |
| 3,355,811 | A |   | 12/1967 | Tailleur ........................ 33/522 |
| 4,025,421 | A |   | 5/1977 | Mueller ...................... 73/865.8 |
| 5,077,909 | A |   | 1/1992 | Cranor ....................... 33/833 |
| 5,481,483 | A | * | 1/1996 | Ebenstein ...................... 356/3 |
| 5,575,075 | A |   | 11/1996 | Sasaki ........................... 33/832 |
| 5,723,797 | A | * | 3/1998 | Dimmick et al. .......... 73/865.8 |
| 6,012,344 | A |   | 1/2000 | Halbo ........................ 73/865.8 |
| 6,415,526 | B1 | * | 7/2002 | Buckner et al. .............. 33/522 |

* cited by examiner

Primary Examiner—G. Bradley Bennett
(74) Attorney, Agent, or Firm—Charles E. Dadswell

(57) ABSTRACT

An apparatus for measuring the alignment of a valve sealed onto a canister comprises hollow lower and upper sections, a mounting platform, and a transducer. The upper and lower interior regions cooperatively define an inner chamber in which the mounting platform is disposed. The transducer is mounted to the upper section and includes a probe extending through the upper section and into the inner chamber. The apparatus is adapted for relative rotational movement between the mounting platform and the upper section. The transducer is responsive to linear translation of the probe and displays a human-readable indication of the alignment of a valve sealed in a canister as the probe moves around the circumference of the top surface of the valve.

3 Claims, 14 Drawing Sheets

FIG. 10A
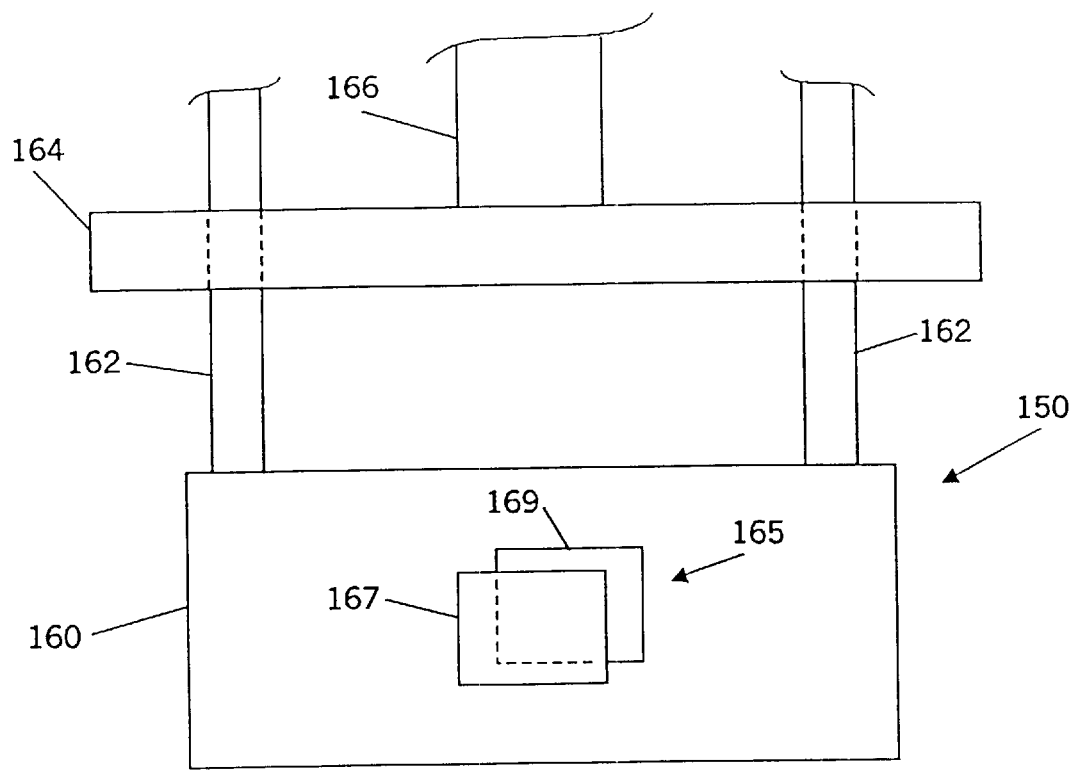
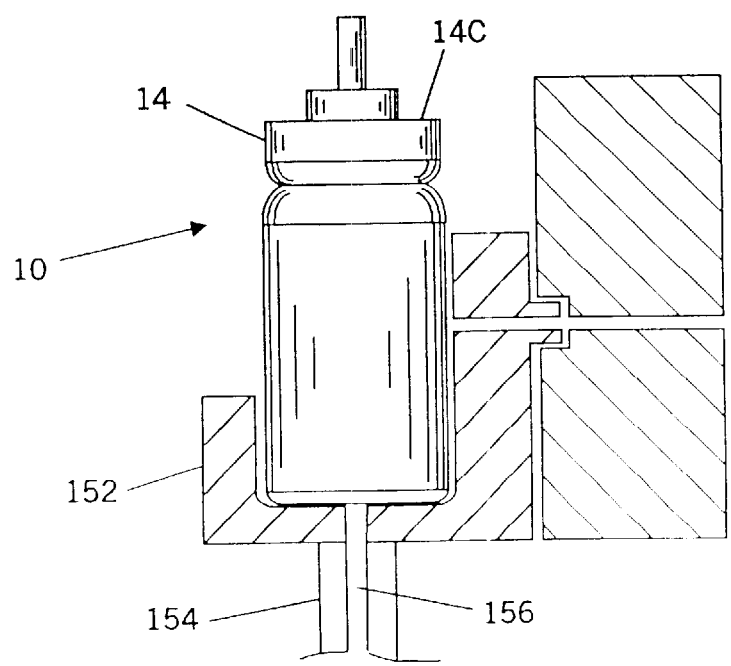

FIG. 10B
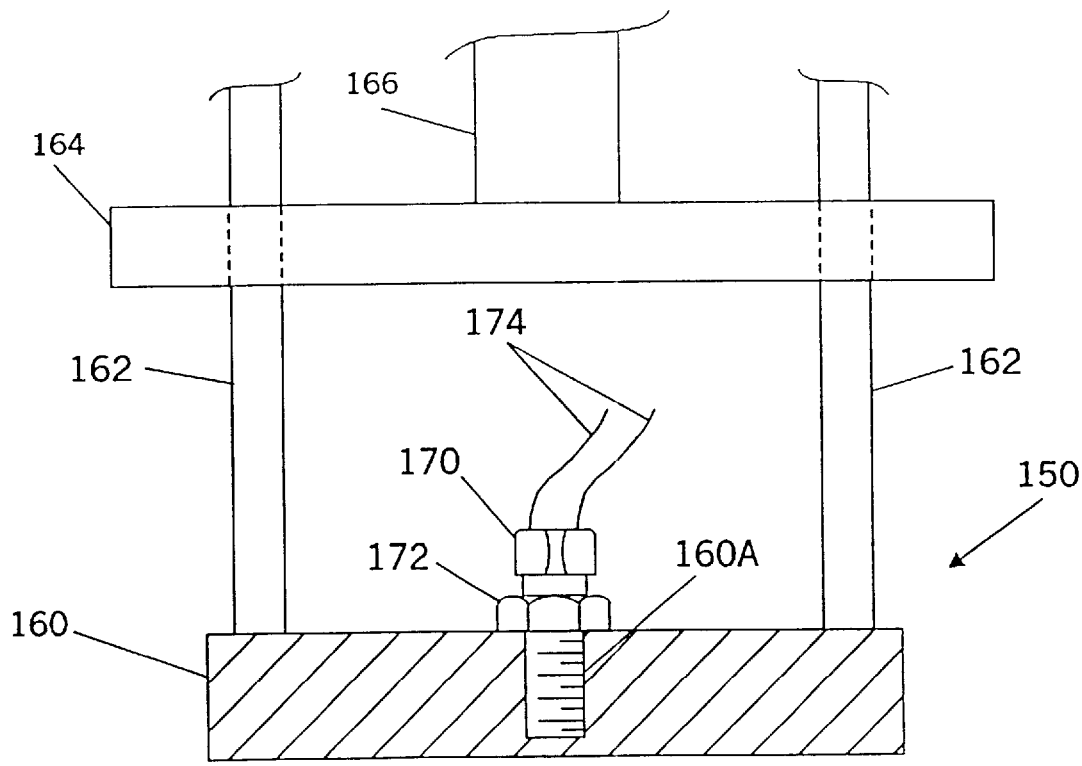
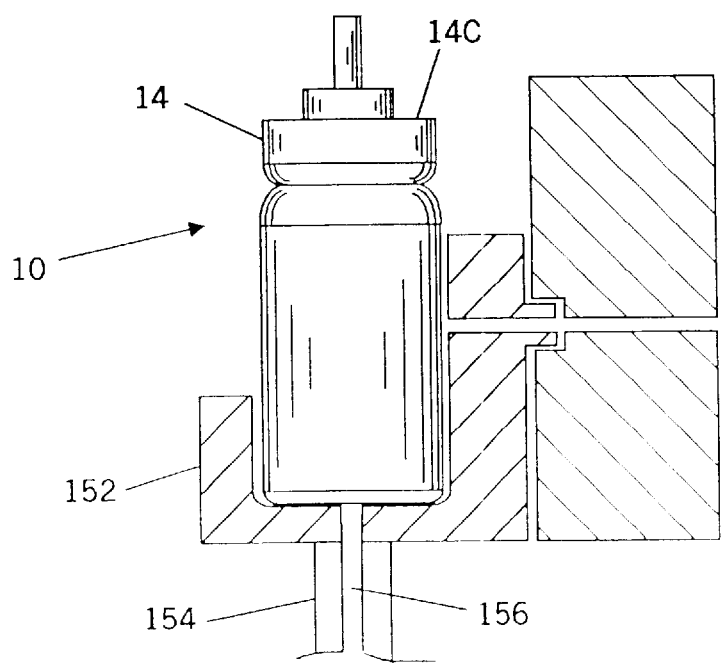

APPARATUS AND METHOD FOR MEASURING ALIGNMENT OF METERED DOSE INHALER VALVES

This application is filed pursuant to 37 CFR 1.53(b) as a continuation patent application of Ser. No. 09/561,232 filed Apr. 28, 2000 now U.S. Pat. No. 6,415,526 in the United States Patent and Trademark office, for which a PCT patent application PCT/US01.13498 was filed Apr. 26, 2001 in the PCT/RO/US

TECHNICAL FIELD

The present invention is generally directed to the manufacturing of sealed canisters containing an operative substance such as a medicine and a propellant. More particularly, the present invention is directed to testing the integrity of the seal of such canisters, especially canisters utilized in metered dose inhaler systems.

BACKGROUND ART

Many types of medicines are provided in fluid form, such as a solution or suspension of particles in a propellant or emulsion, and are adapted for oral inhalation by a patient. As one example, a canister might contain asthma medicine such as fluticasone propionate. During a typical manufacturing process, the canister is sealed with a cap that includes a metering valve. The seal is effected by crimping the valve cap onto the neck of the canister. The canister is then, many times, charged through the valve stem with an aerosol or other propellant.

In order to deliver medicine to the patient, the canister operates in conjunction with an actuator as a system commonly known as a metered dose inhaler (MDI) system. The actuator includes a housing having an open canister-loading end and an open mouthpiece. A nozzle element is disposed within the housing and includes a valve stem-receiving bore communicating with a nozzle orifice. The orifice is aimed toward the mouthpiece. In order to receive a properly metered dosage of medicine from the canister, the patient installs the canister into the actuator through the canister-loading end until the valve stem is fitted into the receiving bore of the nozzle element. With the canister so installed, the opposite end of the canister typically extends to some degree outside the actuator housing. The patient then places the mouthpiece into his or her mouth and pushes downwardly on the exposed canister end. This action causes the canister to displace downwardly with respect to the valve stem, which in turn unseats the valve. Owing to the design of the valve, the design of the nozzle element, and the pressure differential between the interior of the canister and the ambient air, a short burst of precisely metered, atomized medicine is thereby delivered to the patient.

As known to those skilled in the art, the quality of the crimping process by which the valve cap is sealed onto the canister is of utmost criticality. Even a slight defect in the resulting crimp will constitute an improperly sealed valve cap. That is, because of the significant pressure differential between the interior of the canister and the ambient air, the slightest leak will render the canister commercially valueless. By the time the defective canister has been distributed to the patient, most or all of the propellant will have escaped the confines of the canister. As a result, the pressure differential has been eliminated and the canister rendered inoperative.

It would therefore be advantageous to provide a feasible method for identifying and diagnosing problems associated with the canister crimping assemblies employed in MDI production lines. The present invention is provided to address these and other problems associated with the assembly of ends, tops or caps onto open-ended canisters, as well as problems associated with the measurement of height or the determination of levelness for the ends of other types of objects.

DISCLOSURE OF THE INVENTION

The present invention disclosed herein results from an acknowledgment that in order for the valve cap to be crimped onto the canister properly, thus ensuring the integrity of the seal, the valve cap must be accurately aligned onto the canister during the crimping process. It is further acknowledged that accurate alignment, and thus a seal of acceptable quality, can be indicated by measuring the height or the distance of a top surface of the valve cap of an assembled canister with respect to a reference point. By taking several such measurements around a circular line on a flat portion of the top surface of the valve cap, and by comparing those measurements with a predetermined value or range of acceptable values, the levelness of the valve cap can be determined and the integrity of the seal adjudged from the resulting data. The measurements can be taken either by axially rotating the canister and its valve cap with respect to the probing element of a transducer, or by axially rotating the probing element with respect to the valve cap.

The present invention generally provides two approaches to determining the alignment and levelness of the valve cap. In the first approach, a portable, hand-held measuring apparatus is provided for analyzing assembled canisters off-line with regard to the manufacturing process. The first approach is most practicably implemented by employing a micrometer or other transducer that includes a mechanical probe to physically contact the valve cap. In the second approach, a measurement system that includes a measurement station is adapted for integration with the in-line canister assembly process. The second approach is most practicable implemented be employing a non-contacting type of micrometer or transducer. In both approaches, a plurality of standard-sized canisters can be analyzed without changing the set-up or configuration of the apparatus.

In accordance with a first embodiment of the present invention, a measuring apparatus comprises a housing defining an inner chamber therein and a transducer mounted to the housing. The transducer includes a probe that extends into the inner chamber. A mounting platform is disposed within the inner chamber of the housing and is adapted for mounting an object thereon having opposing first and second end surfaces. The measuring apparatus is adapted for relative rotational movement between the mounting platform in the transducer probe so that the probe is caused to contact a portion of the first end surface of the object.

In accordance with another embodiment of the present invention, measuring device comprises a lower section defining a lower interior region, an upper section defining an upper interior region, a mounting platform, and a transducer. The lower section includes a first end surface having an aperture communicating with the lower interior region. The upper section includes first and second end surfaces. The upper section second end surface has an aperture communicating with the upper interior region and extends into the lower interior region of the lower section. The aperture of the upper section second end surface communicates with the lower interior region, and the upper and lower interior regions cooperatively define an inner chamber. The mounting platform is disposed within the inner chamber and is adapted for mounting an object thereon having opposing first and second end surfaces. The transducer is mounted to the upper section and includes a linearly movable probe. The probe extends through the upper interior region and into the inner chamber. The transducer is responsive to a translation of the probe. The apparatus is structurally adapted for relative rotational movement between the mounting platform and the transducer probe so that the probe is caused to contact a portion of the first end surface of the object.

In one of the preferred embodiments according to the present invention, a hollow insert is disposed within the lower section of the measuring device. The insert has an outer lateral surface and an inner lateral surface. When the insert is disposed within the lower section, the outer lateral surface of the insert is adjacent to an inner lateral surface of the lower section. The insert includes a longitudinal slot disposed in parallel with the longitudinal axis and is exposed to the lower interior region of the lower section. A transverse member is attached to an outside lateral surface of the upper section, and extends radially outwardly with respect to the longitudinal axis. The transverse member is slidably disposed in the longitudinal slot.

In another method for determining the levelness of an end surface of an object, a measuring device is provided which comprises a housing defining an inner chamber, a transducer mounted to the housing, and a mounting platform disposed within the inner chamber. The transducer includes a probe extending into the inner chamber. An object including opposed first and second inner surfaces is placed into the inner chamber, and the second end surface of the object is secured onto the mounting platform. The probe is brought into contact with the first end surface of the object. Relative rotational movement is then carried out between the mounting platform and the probe such that the probe travels along a portion of the first end surface of the object.

In another method for determining the levelness of an end surface of an object, a measuring device is provided which comprises a housing including a hollow upper section and a hollow lower section cooperatively defining an inner chamber, a transducer mounted to the housing and including a probe extending into the inner chamber, and a mounting platform disposed within the inner chamber. An object having opposed first and second end surfaces is placed into the inner chamber. The second end surface of the object is secured onto the mounting platform by sliding the upper section into the lower section. The sliding causes a downward displacement of the upper section with respect to the lower section along a central longitudinal axis common to both the upper and lower sections. A distal end of the probe is brought into contact with the first end surface of the object at a point disposed along a circumference of the first end surface. An indication of the levelness of the first end surface of the object is produced by comparing a zero reference point of the probe to a change in displacement of the probe, which displacement change is effected by the contacting of the distal end with the first end surface. The distal end of the probe is then brought into contact with the first end surface at another point disposed along the circumference of the first end surface, and another indication of levelness is produced. This process can be repeated a number of times in order to produce a plurality of indications.

In a further embodiment according to the present invention, a system is provided for detecting an improperly sealed valve of a canister during a canister assembly or filling process. The system comprises a detection station, a conveying device, and a non-contacting measuring device. The conveying device extends through the detection station and includes a movable element. A canister is disposed on the movable element and can be advanced by the movable element through the detection station. The canister includes an open upper canister end sealed by a valve cap having a top surface. The non-contacting measuring device is mounted to the detection station such that it can measure the height of the top surface of the valve cap.

It is therefore an object of the present invention to provide a method and apparatus for measuring the alignment of an end of an object, such as a valve assembled onto a canister.

It is another object of the present invention to provide a method and apparatus for measuring the alignment of a valve assembled onto a plurality of differently sized canisters without having to change the configuration of setup of such apparatus.

It is a further object of the present invention to provide a portable, hand-held apparatus for measuring the alignment of a valve assembled onto a canister.

It is a still further object of the present invention to provide a method and apparatus for measuring the alignment of a valve assembled onto a canister while either axially rotating the canister with respect to a transducer or axially rotating the transducer with respect to the canister.

It is yet another object of the present invention to provide an apparatus for measuring the alignment of a valve assembled onto a canister, wherein the apparatus is integrated with the in-line manufacturing or filling process of the canister.

Some of the objects of the invention having been stated hereinabove, other objects will be evident as the description proceeds, when taken in connection with the accompanying drawings as best described hereinbelow.

BRIEF DESCRIPTION OF THE DRAWINGS

FIG. 10A is a front elevation view of an in-line measuring apparatus according to another embodiment of the present invention; and FIG. 10B is a front elevation view of an in-line measuring apparatus according to a further embodiment of the present invention.

DETAILED DESCRIPTION OF THE INVENTION

Figure 1A:
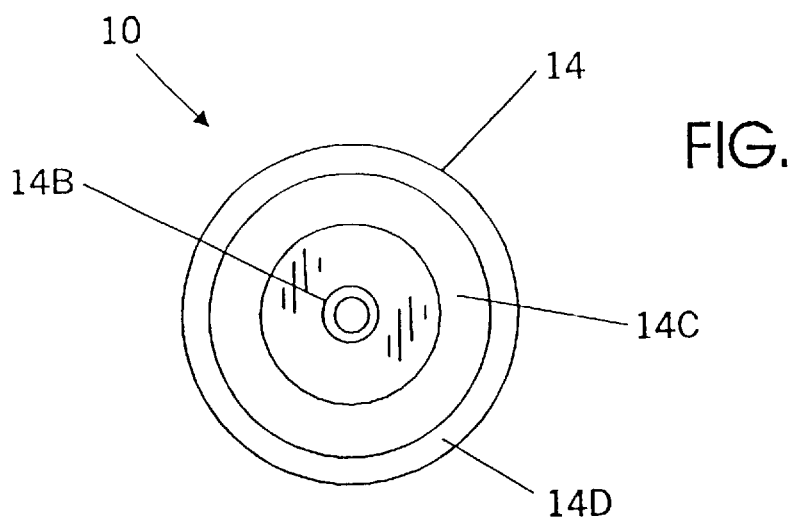
FIG. 1A is a top plan view of the canister of FIG. 1.
Figure 1:
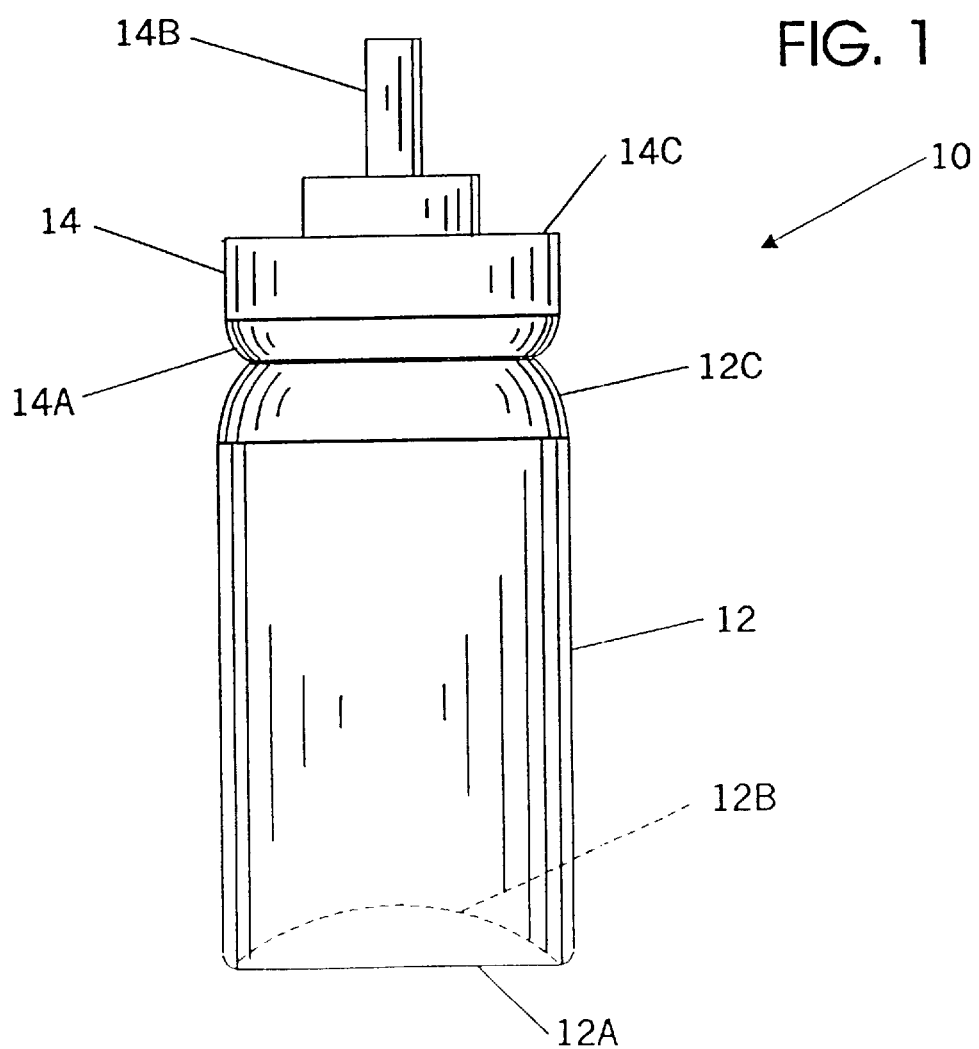
FIG. 1 is a side elevation view of a canister to be measured by a measuring apparatus provided in accordance with the present invention.

FIGS. 1 and 1A illustrate a typical MDI canister generally designated 10. Canister 10 includes a canister body 12 having a typical diameter of 0.87 inches. Canister body 12 is bounded by a closed bottom canister end 12A, which usually has a concave profile 12B (shown in phantom), and an open upper canister end concealed by a valve cap 14. A canister shoulder 12C provides a regional transition from canister body 12 to the upper canister end. Valve cap 14 is sealed over the upper canister end at a crimped section 14A. Valve cap 14 includes a valve stem 14B extending outwardly therefrom. As shown in FIG. 1A, a top surface 14C of valve cap 14 is flat in at least an annular region 14D of valve cap 14. There are three standard sizes for canister 10, which may be referred to as short, medium, and tall. Short, medium and tall canisters 10 have respective heights of 1.54, 1.93, and 2.37 inches. Short canister 10 typically delivers 60 metered doses, medium canister 10 typically delivers 120 doses, and tall canister 10 typically delivers 200 doses.

Figure 2:
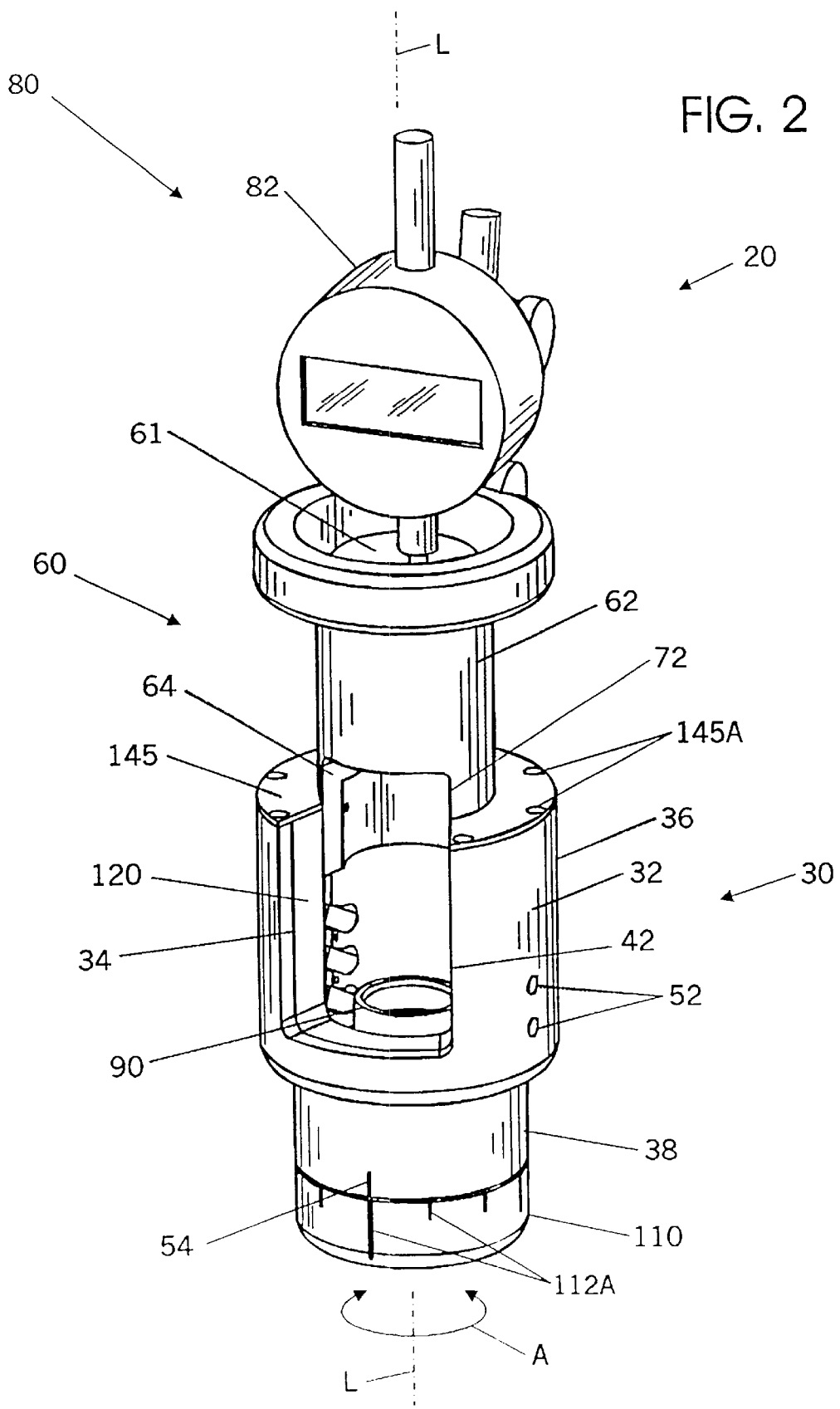
FIG. 2 is a perspective view of a portable measuring apparatus according to one embodiment of the present invention.

Referring to FIG. 2, a preferred embodiment of an off-line MDI valve alignment measuring device generally designated 20 is illustrated in assembled form according to the present invention. Measuring device 20 is shown in its open position. Measuring device 20 includes a lower body generally designated 30, an upper body generally designated 60, a transducer generally designated 80, a mounting platform 90, a rotatable dial or handle 110, and a cylindrical sleeve or insert 120. Lower body 30 and upper body 60 have respective outer lateral surfaces 32 and 62. Each outer lateral surface 32, 62 is shown to be cylindrical, but this is not a requirement. Lower body 30 and upper body 60 also have respective inner lateral surfaces 34 and 64 and hence hollow interiors. Lower body 30 and upper body 60 are disposed coaxially with respect to a central longitudinal axis L common to both lower and upper bodies 30 and 60. Lower body 30 further includes a main section 36 and a reduced-diameter section 38. As described in more detail below, upper body 60 is slidably mounted within the interior of lower body 30 along longitudinal axis L.

Platform 90 for mounting canister 10 within measuring device 20 is disposed within the interior of lower body 30, and is accessible through a side port formed by the combination of a cut-out section 42 of lower body 30 and a cut-out section 72 of upper body 60. As described in more detail below, platform 90 rotates with handle 110 disposed below reduced-diameter section 38 of lower body 30. The rotation of platform 90 and handle 110 is about longitudinal axis L, and is generally indicated by arrow A. Insert 120, also described below, is disposed within lower body 30 and is secured therein by means of an annular cap ring 145, holes 145A, and appropriate fastening means in holes 145A such as screws (not shown).

Figure 3:
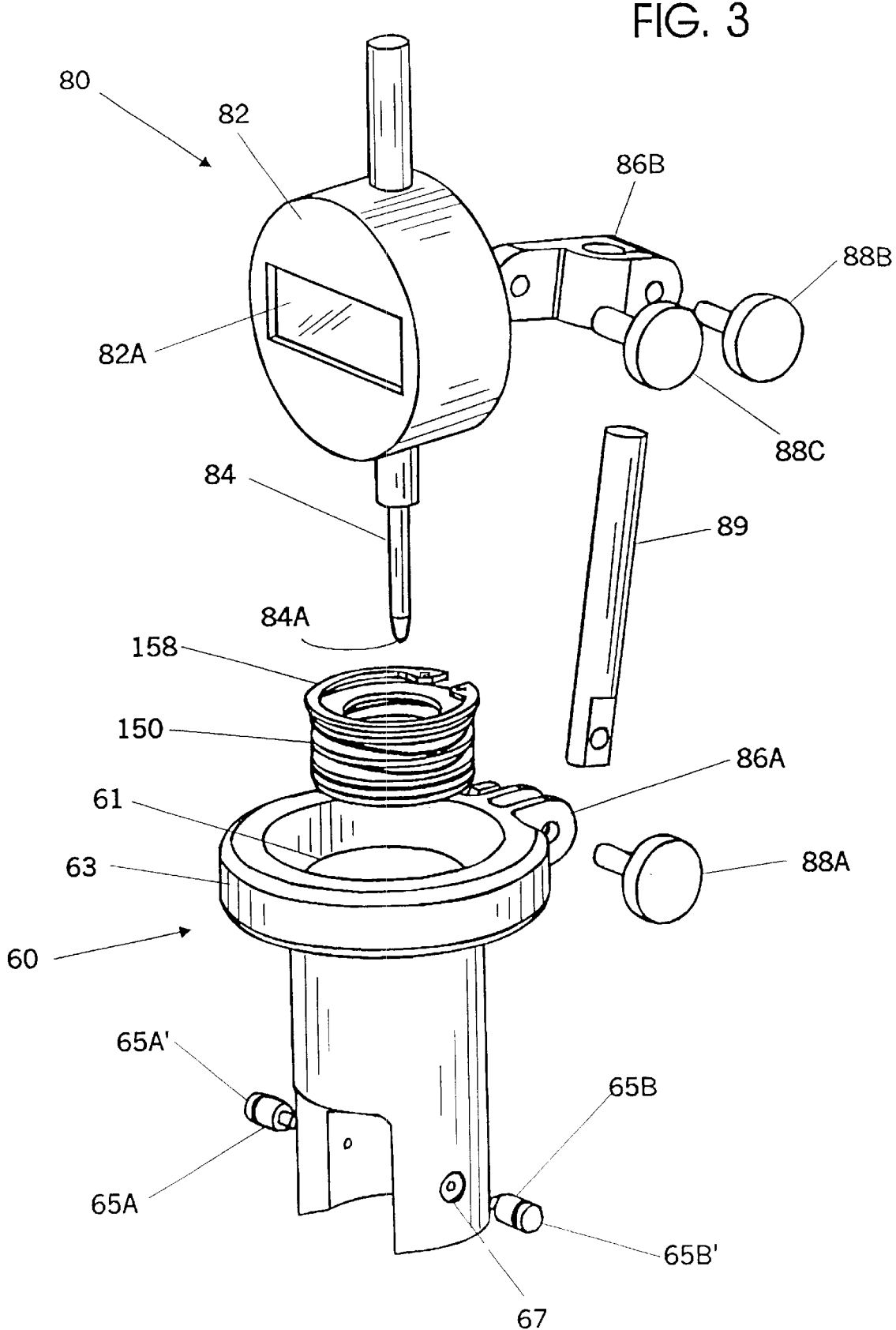
FIG. 3 is an exploded perspective view of upper components included with the measuring apparatus of FIG. 2.

Referring to FIG. 3, transducer 80 includes a housing 82 and a spring-loaded probe 84 depending downwardly therefrom. The distal end of probe 84 includes a roller-ball tip 84A. Transducer 80 is preferably a micrometer equipped with a digital readout such as a liquid crystal display 82A. A suitable, off-the-shelf micrometer is available from MITUTOYO and designated as Model No. 543–253. Transducer 80 is designed to measure the magnitude and direction of the linear movement of probe 84, and to convert that measurement into a representative digital value for display at readout 82A. Transducer 80 is situated above upper body 60 such that probe 84 can extend through an opening 61 at the top of upper body 60 into the interior thereof. For this purpose, transducer 80 is preferably secured to a flanged portion 63 of upper body 60 by employing a combination of devises 86A and 86B, screws 88A, 88B and 88C, and an extension rod 89. In this manner, one or more screws 88A–88C can be loosened and extension rod 89 manipulated in order to adjust the position of transducer 80 over upper body 60 and consequently the position of probe 84 within measuring device 20. In addition, transducer 80 can be removed from measuring device 20 in order to replace batteries, to service transducer 80, or to perform calibrations if necessary.

A pair of roller-type cam followers 65A and 65B with rollers 65A' and 65B' are mounted in countersunk holes 67 of upper body 60 by known means. Cam followers 65A and 65B interact with insert 120 in a manner described below. Also shown in FIG. 3 is a three-tiered disk spring 150 and C-clip 158, which are disposed coaxially within the interior of upper body 60. Referring to the cut-away view of FIG. 6, an annular collar 66 extends from inner lateral surface 64 of upper body 60 radially inwardly toward longitudinal axis L. Collar 66 has an upper shoulder 66A on which disk spring 150 rests. Disk spring 150 is secured within the interior of upper body 60 between upper shoulder 66A and C-clip 158. C-clip 158 is disposed in a fixed position through its expansion into a circumferential groove 68 located on inner lateral surface 64 of upper body 60. The function of disk spring 150 is described below.

Figure 4:
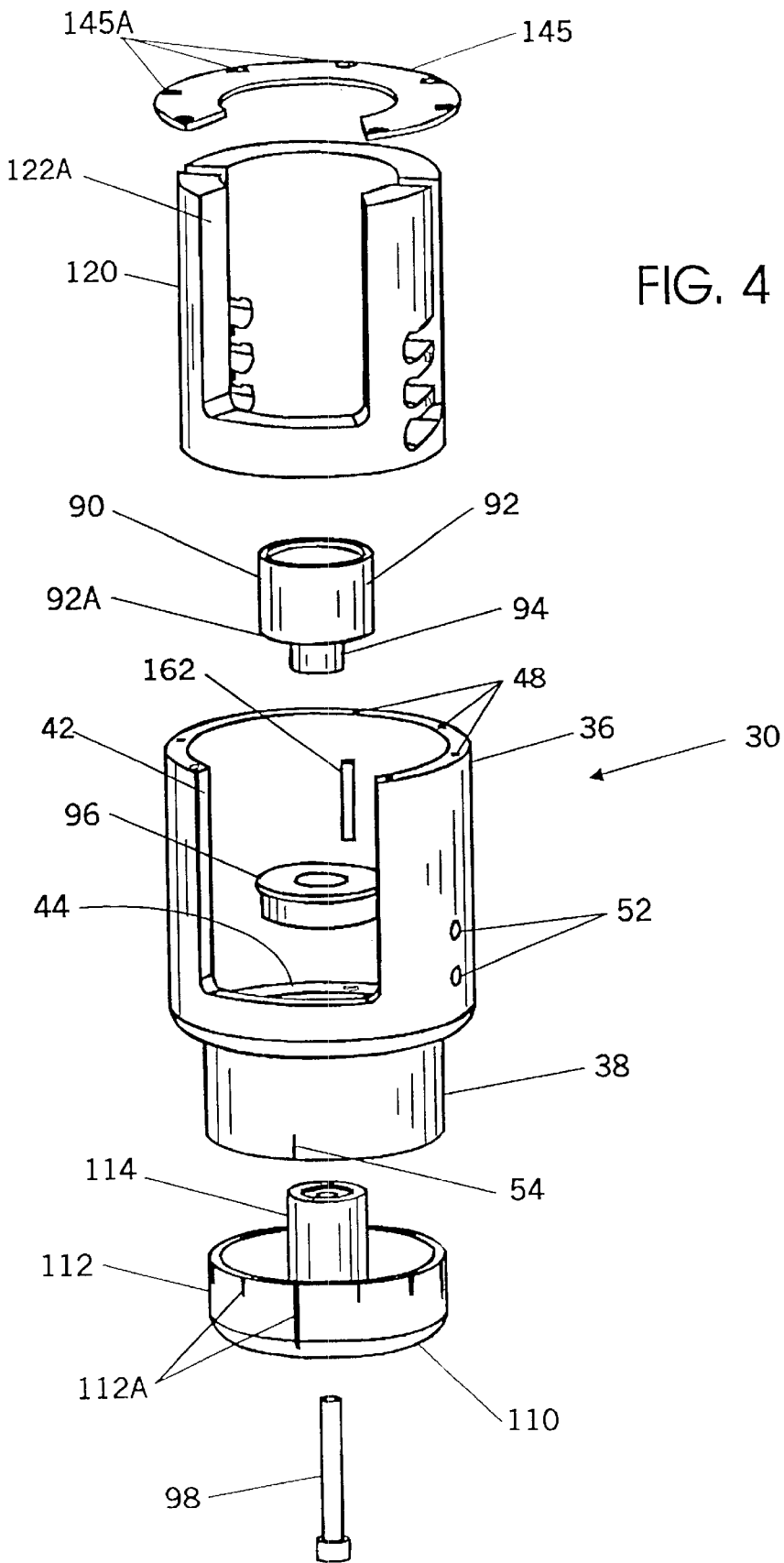
FIG. 4 is an exploded perspective view of lower components included with the measuring apparatus of FIG. 2.
Figure 5:
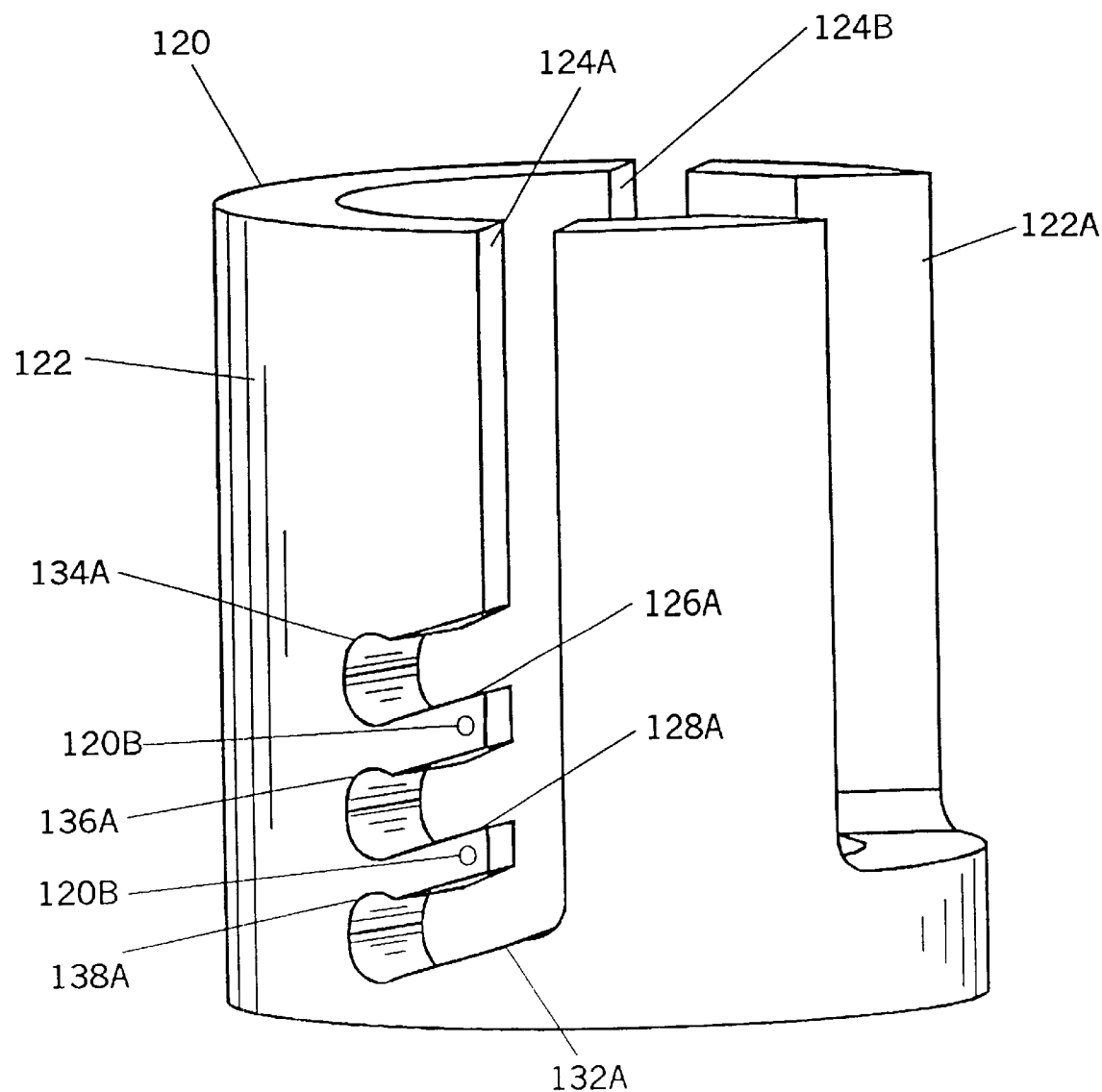
FIG. 5 is a perspective view of an insert provided with the measuring apparatus of FIG. 2.
Figure 6:
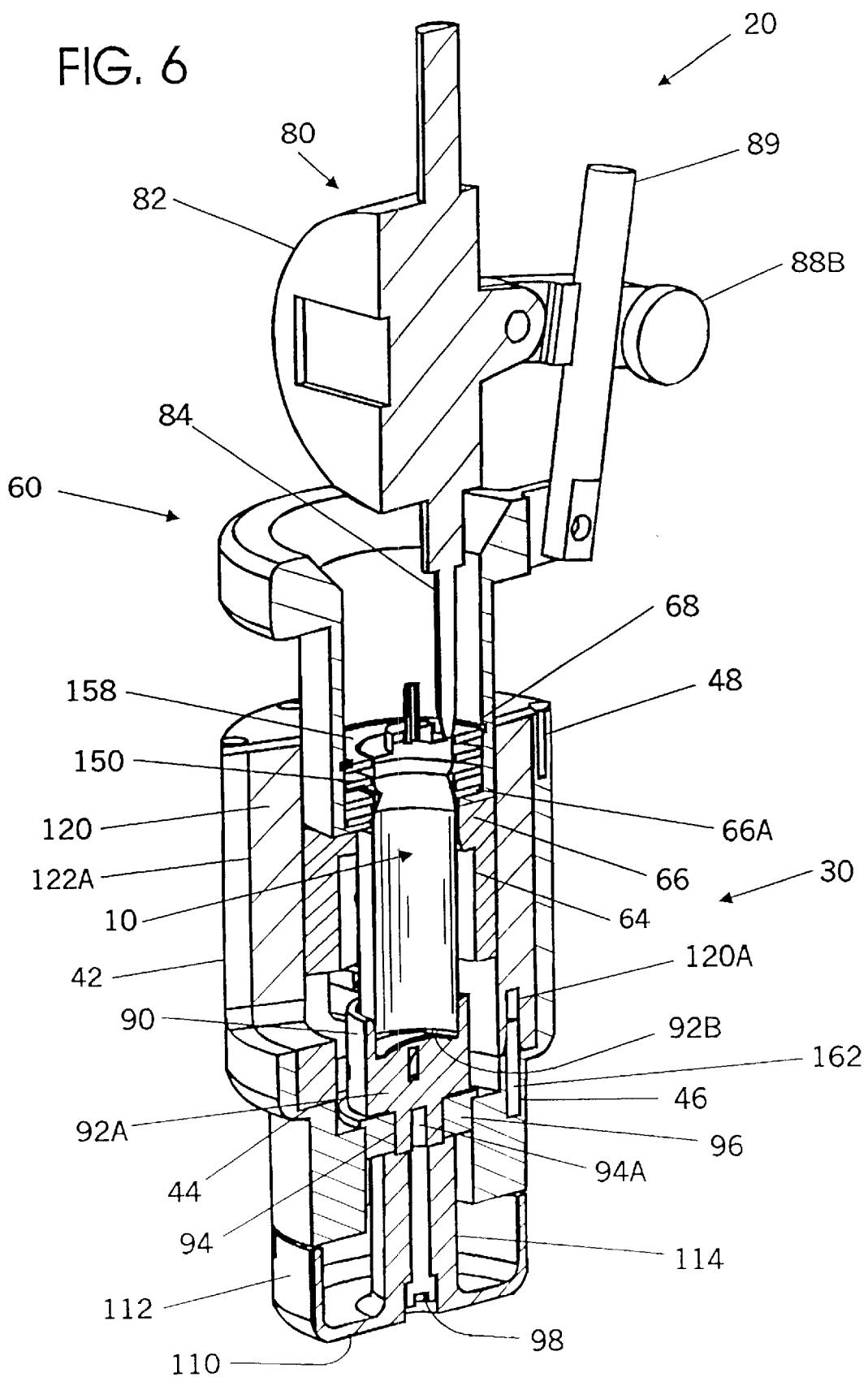
FIG. 6 is a perspective cut-away view of the measuring apparatus of FIG. 2 illustrated with a canister loaded therein.

Referring to FIGS. 4 and 6, insert 120 is secured within lower body 30 between cap ring 145 and an annular shoulder 44 located at the transition between main section 36 and reduced-diameter section 38. Insert 120 can be secured by aligning a cut-out section 122A thereof with cut-out section of lower body 30, disposing a dowel or shim 162 in a recess 120A of insert 120 and a recess 46 of reduced-diameter section 38, and aligning countersunk holes 145A of cap ring 145 with corresponding threaded bores 48 of main section 36 and threading screws (not shown) into bores 48. In order to provide structural reinforcement for insert 120, side holes 52 of lower body 30 can be aligned with side holes 120B of insert 120 (see FIG. 5), and screws (not shown) threaded through side holes 52 and into side holes 120B. Although only one pair of side holes 120B are shown in FIG. 5 and only one pair of side holes 52 are shown in FIGS. 2 and 4, additional pairs of corresponding side holes 120B and side holes 52 (not shown) could be provided around the periphery of insert 120 and lower body 30, respectively.

Handle 110 shown in FIGS. 4 and 6 includes a cap portion 112 and a hollow cylindrical portion 114 centrally disposed within reduced-diameter section 38 of lower body 30. Cap portion 112 can include a plurality of hash marks 112A, which are either embossed or grooved. As shown in FIG. 2, handle 110 can be rotated to align hash marks 112A with a reference mark 54 provided on outside lateral surface 32 of lower body 30 at reduced-diameter section 38.

Platform 90 is preferably cup-shaped with an outer wall 92 and a base 92A. Base 92A has a convex profile 92B (see FIG. 6) to conform with concave profile 12B of bottom canister end 12A of canister 10. Platform 90 includes a lower plug portion 94 having a blind threaded bore 94A. Platform 90 is seated on a ball bearing 96 fitted into reduced-diameter section 38 of lower body 30. Platform 90 is installed into measuring device 20 by extending lower plug portion 94 through the bore of ball bearing 96, extending a mounting stud such as an axial bolt 98 through hollow cylindrical portion 114 of handle 110, and threading axial bolt 98 into blind bore 94A of lower plug portion 94. As a result, platform 90 is secured to handle 110 and rotates with handle 110 about longitudinal axis L.

Referring to FIG. 5, insert 120 includes a cylindrical wall 122 having cut-out section 122A which cooperates with cut-out section 42 of lower body 30 to form the side port of measuring device 20. Insert 120 is preferably constructed of glass-filled nylon, although such a choice of materials is not a limitation of the present invention. Insert 120 also includes a pair of diametrically opposed, parallel longitudinal tracks or slots 124A and 124B cut out of cylindrical wall 122 of insert 120. A plurality of transitional slots branch off each corresponding longitudinal slot 124A and 124B. There are preferably three transitional slots for each longitudinal slot 124A and 124B. Thus, longitudinal slot 124A is associated with an upper transitional slot 126A, a medial transitional slot 128A, and a lower transitional slot 132A. Each transitional slot 126A, 128A and 132A is oriented at a downward angle, which orientation could take a helical path if desired. There also exist corresponding upper, medial and lower transitional slots which branch off longitudinal slot 124B, although these transitional slots are not shown in FIG. 5. For clarity, the corresponding pairs of upper, medial and lower transitional slots of longitudinal slots 124A and 124B are collectively referenced hereinafter as upper transitional slots 126, medial transitional slots 128, and lower transitional slots 132. Insert 120 further includes a plurality of terminal slots such as an upper terminal slot 134A, a medial terminal slot 136A, and a lower terminal slot 138A. Each terminal slot 134A, 136A and 138A branches off the lower end of its corresponding transitional slot 126A, 128A and 132A at an upward angle. Although not shown, upper, medial and lower terminal slots are similarly associated with the transitional slots of longitudinal slot 124B. The corresponding pairs of upper, medial and lower terminal slots associated with longitudinal slots 124A and 124B are collectively referenced hereinafter as upper terminal slots 134, medial terminal slots 136, and lower terminal slots 138.

Accordingly, when insert 120 is installed into lower body 30, longitudinal slots 124A and 124B, transitional slots 126, 128 and 132 and terminal slots 134, 136 and 138 cooperate with inner lateral surface 34 of lower body 30 to form grooved paths in which cam followers 65A and 65B of upper body 60 respectively travel during movement of measuring device 20 from an open position to a closed position. It should be noted that measuring device 20 according to the present invention is particularly adapted to measure canisters 10 of either the standard short, medium or tall size. Thus, in the exemplary embodiment described herein, three paths through which cam followers 65A and 65B can travel are provided. The particular path taken depends upon the size of canister 10 to be analyzed. Each path includes longitudinal slots 124A and 124B. When a tall canister 10 is loaded into measuring device 20, a first path is characterized as following longitudinal slots 124A and 124B downwardly, branching off longitudinal slots 124A and 124B to progress along upper transitional slots 126, and terminating in upper terminal slots 134. When a medium canister 10 is loaded, a second path is characterized as following longitudinal slots 124A and 124B downwardly, branching off longitudinal slots 124A and 124B to progress along medial transitional slots 128, and terminating in medial terminal slots 136. When a short canister 10 is loaded, a third path is characterized as following longitudinal slots 124A and 124B downwardly, branching off longitudinal slots 124A and 124B to progress along lower transitional slots 132, and terminating in lower terminal slots 138. As described in more detail below, it will be seen that insert 120 with its slotted configuration serves as a cam cylinder for cam followers 65A and 65B.

It will be understood that the number of slots provided by insert 120 could be varied without departing from the scope of the present invention. For example, measuring device 20 could be adapted to measure canister 10 of only a single height, in which case insert 120 would provide a single path defined by longitudinal slots 124A and 124B, one pair of transitional slots 126, 128 or 132, and one pair of terminal slots 134, 136 or 138. In another example, measuring device 20 could be adapted to measure more than three sizes of canisters 10, in which case insert 120 would provide more than three paths.

As an alternative to providing insert 120, lower body 30 could itself serve as the cam cylinder for cam followers 65A and 65B. In such a case, longitudinal slots 124A and 124B, transitional slots 126, 128 and 132, and terminal slots 134,136 and 138 would be respectively be replaced by similarly configured longitudinal grooves, transitional grooves and terminal grooves located on inner lateral surface 34 of lower body 30.

As a further alternative, insert 120 could be provided with longitudinal slots 124A and 124B but without transitional slots 126, 128, and 132 and terminal slots 134, 136, and 138. Or, where insert 120 is not utilized, lower body 30 could be provided with longitudinal grooves but without transitional and terminal grooves. In such cases, some type of releasable latch or catch arrangement could be substituted such that upper body 60 would slide downwardly into lower body 60 and lock onto canister 10 at a vertical position dependent on the height of canister 10.

Figure 7A:
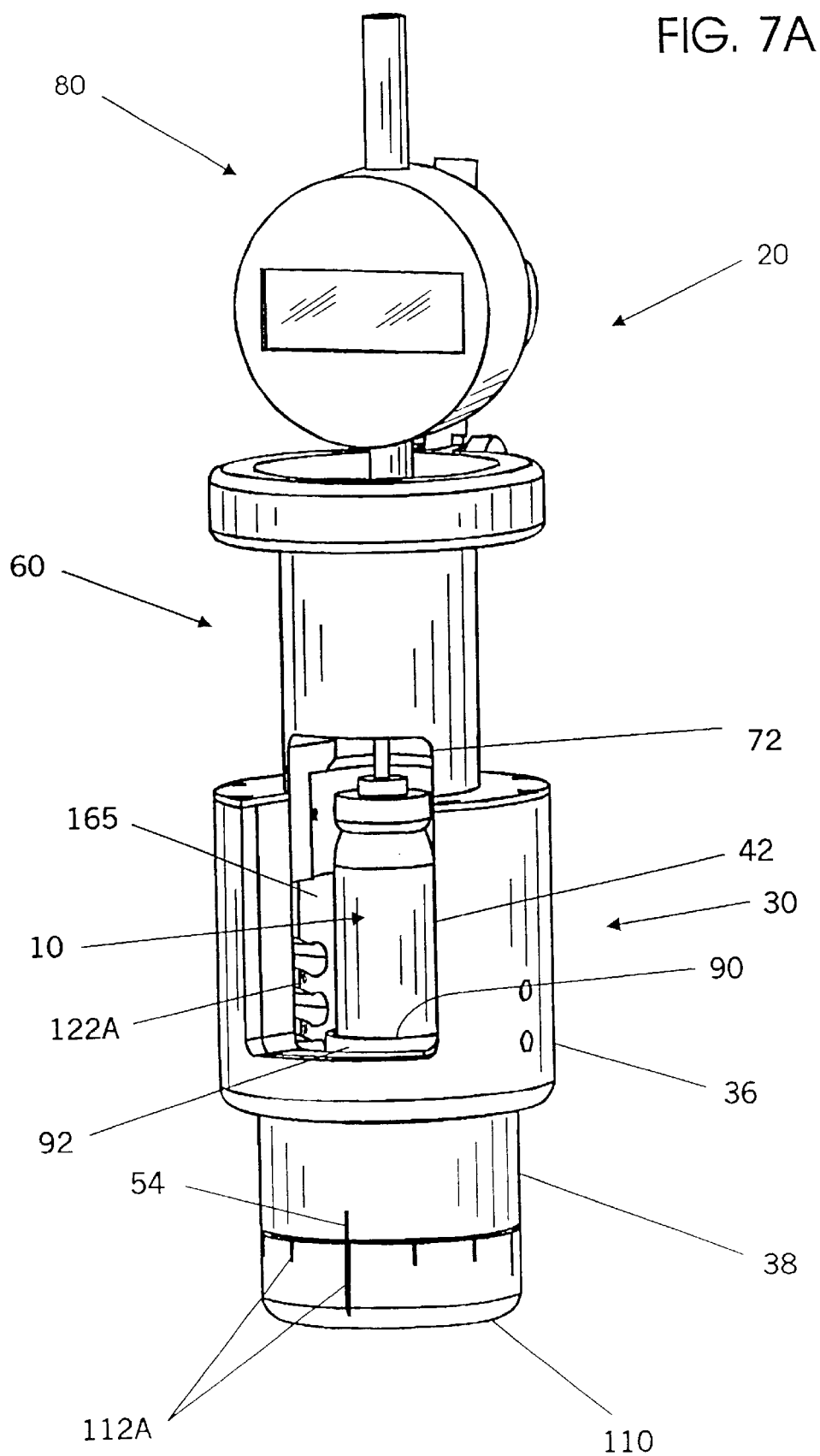
FIG. 7A is a perspective view of the measuring apparatus of FIG. 2 illustrated in its open position with a canister loaded therein.
Figure 7B:
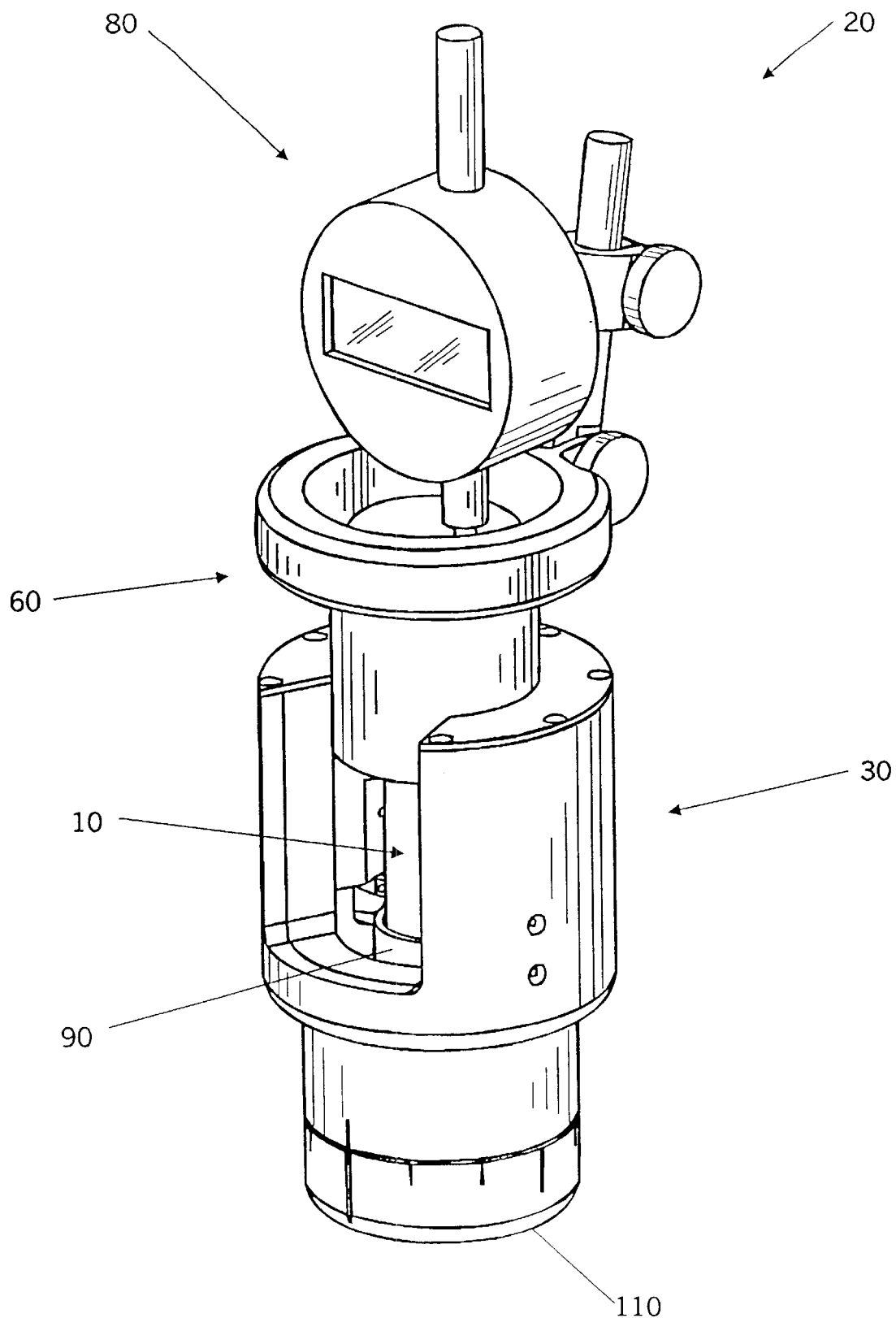
FIG. 7B is a perspective view of the measuring apparatus of FIG. 2 illustrated in its closed position with a canister loaded therein.
Figure 8:
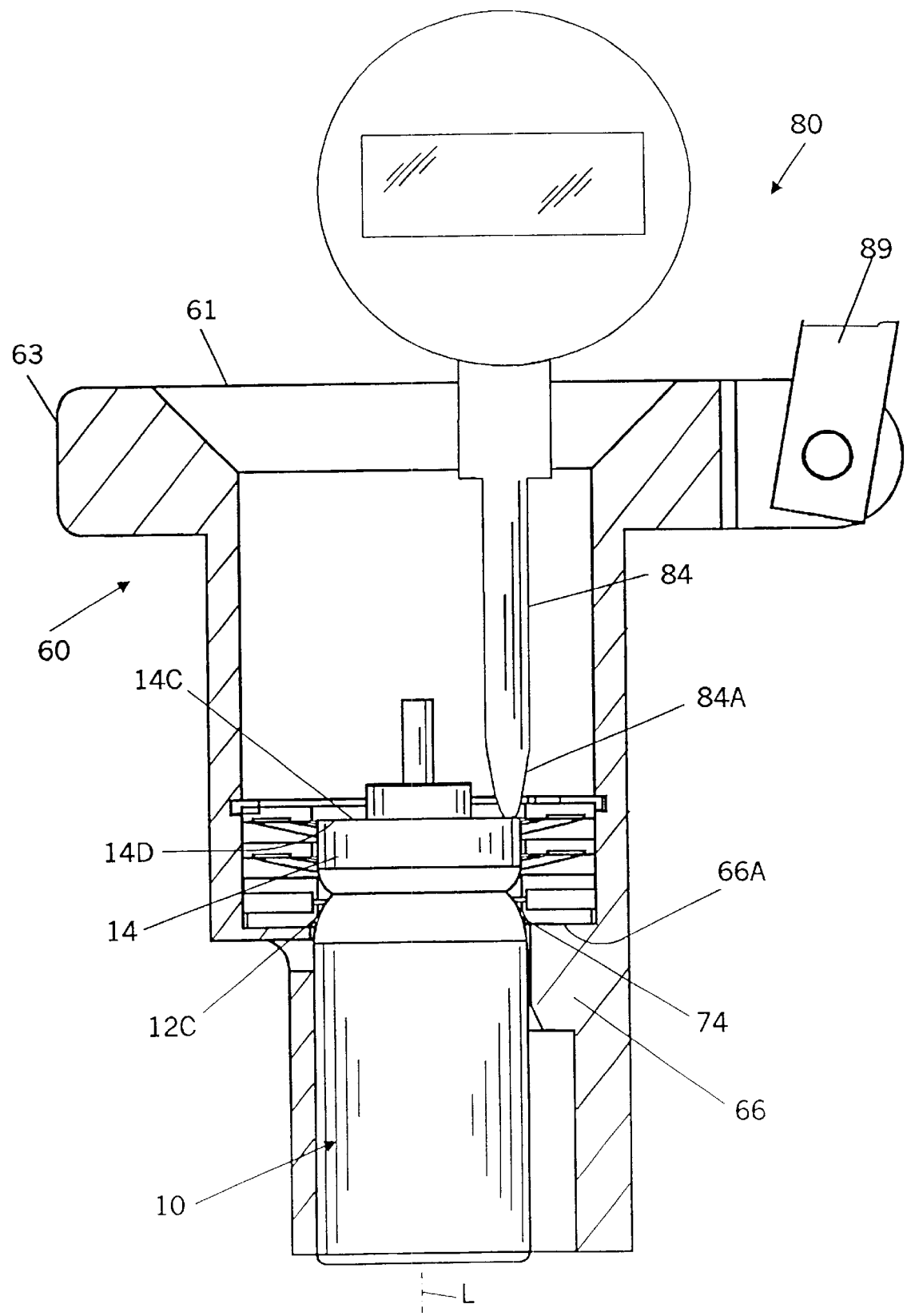
FIG. 8 is a partially cut-away view of an upper portion of the measuring apparatus of FIG. 2 illustrated with a canister loaded therein.

The operation of measuring device 20 will now generally be described with particular reference to FIGS. 6–8. Referring to FIG. 7A, measuring device 20 is shown in its open position. Canister 10 has been loaded into an inner chamber 165 of measuring device 20 defined by the respective interiors of upper body 60 and lower body 30. In the open position, the side port defined by respective cut-out sections 42, 72 and 122A preferably has a large enough area to enable canister 10 to be loaded onto platform 90 in inner chamber 165, although some degree of tilting of canister 10 is acceptable in order for valve stem 14B to clear cut-out section 72 of upper body 60 and outer wall 92 of platform 90. Once canister 10 has been loaded, upper body 60 is slid axially downwardly into lower body 30 and onto canister 10. Upper body 60 is then rotated in the direction of transitional slots 126A, 128A or 132A, of insert 120, until measuring device 20 assumes the closed, locked position illustrated in FIG. 7B.

Referring to FIG. 6, after measuring device 20 reaches its closed position, canister 10 is locked in place and the compressive forces imparted by disk spring 150 act to secure canister 10 in frictional contact with base 92A and profile 92B of platform 90. Hence, in the closed position, rotation of handle 110 (and thus platform 90) causes canister 10 to rotate as well.

Referring to the detailed view of FIG. 8, an annular, chamfered section 74 of upper body 60 rests on canister shoulder 12C when canister 10 is in its locked position. In addition, roller-ball tip 84A of probe 84 is spring-biased into contact with annular region 14D of top surface 14C of valve cap 14. Canister 10 is then measured by rotating handle 110 about longitudinal axis L. Rotation of handle 110 in turn rotates canister 10 with respect to probe 84. If at any point during rotation top surface 14C of valve cap 14 is not level, probe 84 will displace upwardly or downwardly. Transducer 80 registers changes in displacement of probe 84 as indications of deviations in the height of top surface 14C of valve cap 14. Excessive out-of-level measurements indicate problems with the crimping process employed during assembly of canister 10.

It should be noted that before measuring device 20 is employed to take measurements of actual production-run canisters 10, a similarly sized "calibration canister" can first be loaded into measuring device 20 in order to properly obtain a zero reference position for probe 84 of transducer 80. Moreover, at some point before measurements of canister 10 are taken, handle 110 can initially be rotated to align hash marks 112A with reference mark 54 to define a starting datum point for analysis.

As an alternative to taking measurements of canister 10 by rotating canister 10 with respect to probe 84, probe 84 could be adapted to rotate with respect to canister 10. In this alternative embodiment, mounting platform 90 would be fixedly disposed within lower body 30 and flanged portion 63 of upper body 60 would be rotatably mounted to upper body 60. Thus, flanged portion 63 would take the form of a rotary member and serve as a substitute for handle 110. Extension rod 89 could then be used as a handle to rotate transducer and thus probe 84. This alternative, however, is less preferred as it renders display 82A of transducer 80 more difficult to read since display 82A would be moving while transducer 80 takes measurements.

Figure 9A:
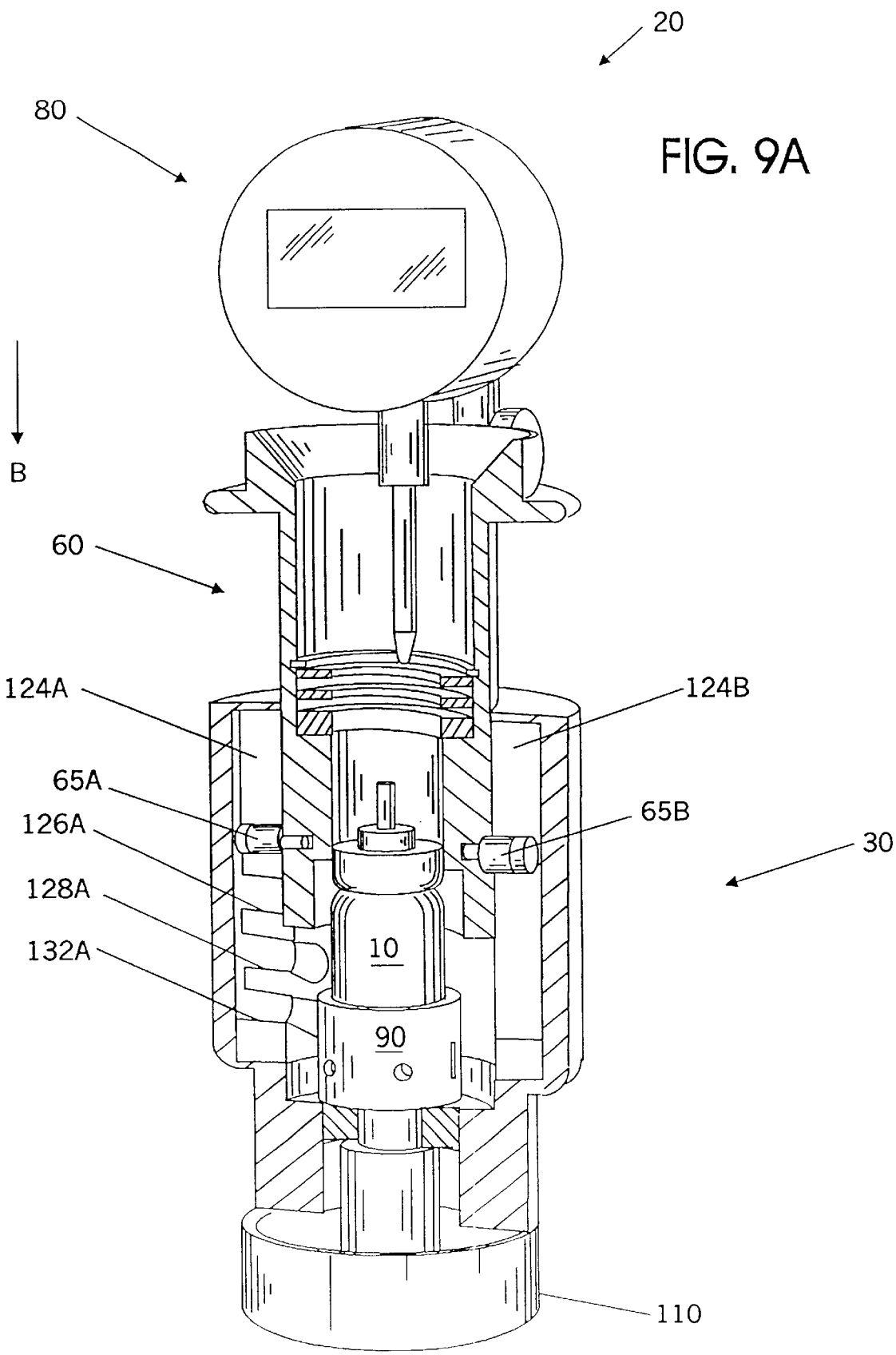
FIGS. 9A, 9B and 9C are partially cut-away views of the measuring apparatus of FIG. 2 respectively showing sequential positions taken by the measuring apparatus while a canister is being secured into a locked position therein.
Figure 9B:
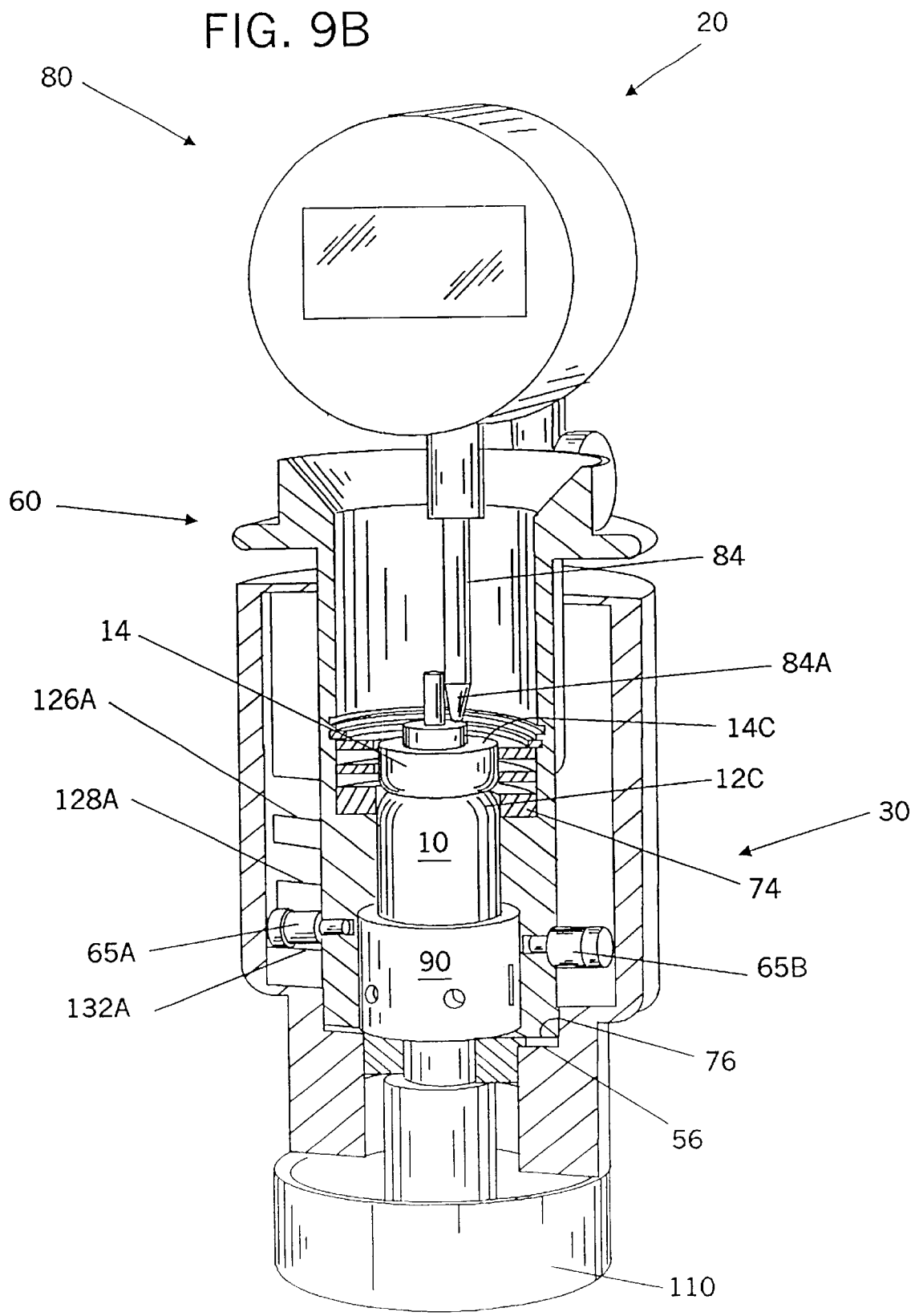
Figure 9C:
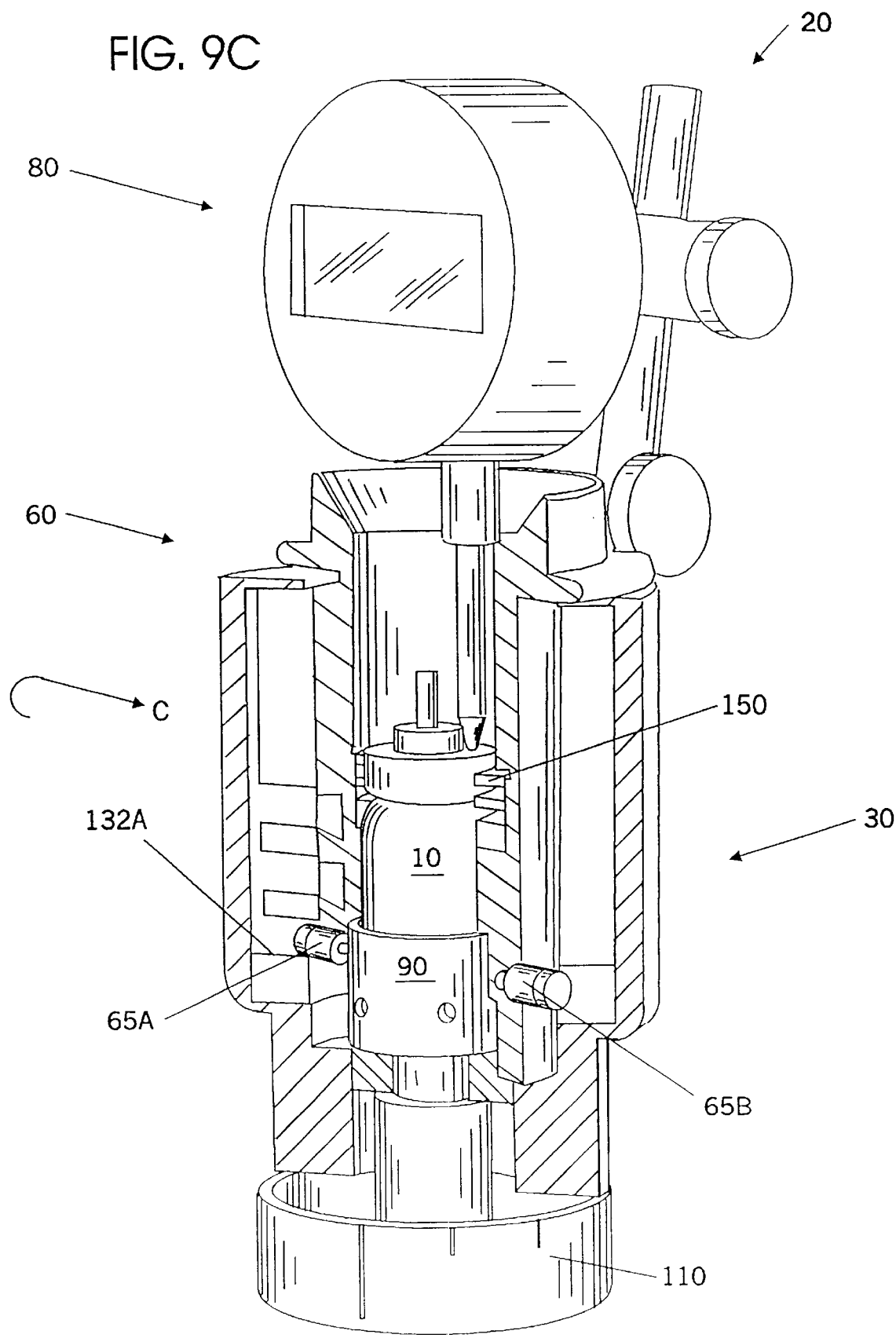

Referring to FIGS. 9A–9C, the sequence for locking short-sized canister 10 into measuring device 20 is illustrated. For short canisters 10, cam followers 65A and 65B take the first path described hereinabove. Accordingly, in FIG. 9A upper body 60 has begun its descent into lower body 30 in the general direction indicated by arrow B, and cam followers 65A and 65B are traveling in the portion of longitudinal slots 124A and 124B above transitional slots 126, 128 or 132. In FIG. 9B, upper body 60 has been pushed further downwardly into lower body 30 to a point where chamfered section 74 has almost made contact with canister shoulder 12C, a bottom end surface 76 of upper body 60 has almost made contact with a corresponding shoulder base 56 of lower body 30, cam followers 65A and 65B are almost fully adjacent to their corresponding lower transitional slots 132, and roller-ball tip 84A of probe 84 has contacted or is about to contact top surface 14C of valve cap 14.

Referring to FIG. 9C, as upper body 60 is rotated or twisted, cam followers 65A and 65B travel along their corresponding lower transitional slots 132, thereby forcing upper body 60 further downwardly onto canister 10. A lower portion of upper body 60 has been removed in FIG. 9C in order to best show the position of cam follower 65A. The twisting direction taken by cam followers 65A and 65B is generally indicated by arrow C. Disk spring 150 simultaneously begins to be compressed, thus pushing canister 10 downwardly and ensuring that canister 10 is properly seated on platform 90. Cam followers 65A and 65B then enter their corresponding lower terminal slots 138 (not specifically shown in FIG. 9C). Because lower terminal slots 138A are angled slightly upwardly with respect to lower transitional slots 132 (see FIG. 5) and disk spring 150 maintains its compressive force on canister 10, cam followers 65A and 65B (and accordingly canister 10 and measuring device 20) are locked in place in the closed position of measuring device 20.

Referring to FIGS. 10A and 10B, a preferred embodiment of an in-line MDI valve alignment measuring system or station generally designated 150 is illustrated. Canister 10 travels along its assembly line by means of a movable member 152 of a conveying device in accordance with known technology. Measuring system 150 includes a transducer head 160 operatively situated by conventional means above movable member 152. Transducer head 160 can be lowered toward canister 10 to be measured through the use of guide rods 162.

In FIG. 10A, transducer head 160 includes a non-contacting transducer in the form of a laser micrometer generally designated 165, which includes an emitter element 167 and a receiver element 169. Laser micrometer 165 takes measurements of the distance from a reference point to top surface 14C of valve cap 14 by directing a light beam from emitter element 167 toward top surface 14C and receiving at receiver element 169 the resultant light beam reflected off top surface 14C. It will be understood that an infrared transducer could be substituted for laser micrometer 165.

In FIG. 10B, transducer head 160 includes an inductive-type distance transducer 170. Inductive transducer 170 is threaded through a nut 172 into a blind counterbored opening 160A in transducer head 160, and includes electrical leads 174 to output a voltage signal proportional to the distance between inductive transducer 170 and top surface 14C of valve cap 14.

Referring to both FIGS. 10A and 10B, a plurality of measurements can be taken by axially rotating transducer head 160 with respect to canister 10. This can be accomplished by mechanically linking transducer head 160 to a turntable 164 attached to a rotating shaft 166. Alternatively, movable member 152 of the conveying device in FIGS. 10A or 10B could take the form of a platform 152 rotatable about a shaft 154. In this case, canister 10 could be loaded into the platform from the conveying device and held in place by a vacuum line 156. Transducer 165 or 170 could remain stationary and take measurements while platform 152 rotates.

It will be understood that various details of the invention may be changed without departing from the scope of the invention. Furthermore, the foregoing description is for the purpose of illustration only, and not for the purpose of limitation—the invention being defined by the claims.

What is claimed is:

1. A system for detecting an improperly sealed valve of a canister during a canister assembly or filling process, the system comprising:

(a) a detection station;

(b) a conveying device extending through the detection station and including a movable element;

(c) a canister disposed on the movable element of the conveying device and adapted to be advanced by the movable element through the detection station, the canister including an open upper canister end sealed by a valve cap, the valve cap including a top surface; and (d) a non-contacting measuring device mounted to the detection station and adapted to measure the height of the top surface of the valve cap.

2. The system according to claim 1 wherein the non-contacting measuring device includes an emitter element and a receiver element, the emitter element adapted to emit a light source towards the top surface of the valve cap, and the receiver element adapted to receive a reflected light source reflected from the top surface.

3. A method for detecting an improperly sealed valve of a canister during a canister assembly or filling process comprising the steps of:

(a) providing a detecting station in operative communication with a conveying device to enable transport of a canister of a canister process line to the detection station, the canister sealed by a valve having a top surface;

(b) mounting a non-contacting measuring device at the detection station; and (c) causing the conveying device to advance the canister to a location of the detection station wherein the non-contacting measuring device takes one or more measurements of the top surface of the valve.

* * * * *